United States Patent [19]

Gordon

[11] 4,359,453

[45] Nov. 16, 1982

[54] ATHEROSCLEROSIS TREATMENT METHOD

[76] Inventor: Robert T. Gordon, 4936 W. Estes, Skokie, Ill. 60076

[21] Appl. No.: 894,504

[22] Filed: Apr. 7, 1978

[51] Int. Cl.³ .................. A61K 43/00; A61K 49/00; G01T 1/00
[52] U.S. Cl. ........................................ 424/1; 128/1.1; 128/1.3; 424/1.5; 424/9
[58] Field of Search ............... 128/1 R, 1.1, 399, 404, 128/1.3, 1.5, 214 R; 424/1, 9, 1.5

[56] References Cited

U.S. PATENT DOCUMENTS

| | | | |
|---|---|---|---|
| 3,474,777 | 10/1969 | Figge et al. | 424/1 |
| 4,106,488 | 8/1978 | Gordon | 128/1 R |
| 4,255,492 | 3/1981 | Audran et al. | 428/694 |
| 4,303,636 | 12/1981 | Gordon | 424/1 |

Primary Examiner—Leland A. Sebastian
Attorney, Agent, or Firm—Lalos, Leeds, Keegan, Lett & Marsh

[57] ABSTRACT

A treatment of atherosclerosis by the application of external electromagnetic energy capable of the generation of heat and biophysical alterations in intracellular particles and particles within atherosclerotic plaques to induce resolution of the atherosclerotic plaques. This process allows for the selective treatment of the atherosclerotic plaque without damaging the normal blood vessel by the compartmentalized alteration of biophysical properties within the atherosclerotic lesion.

The process comprises introducing minute particles into the interior of atherosclerotic plaques and the cells involved in the lesion. These particles being injected intravenously while suspended in an appropriate solution are of a size generally having a diameter of approximately 1 micron or less and one of a material with properties such as ferromagnetic, paramagnetic or diamagnetic so as to be inductively heated when subjected to a high frequency alternating electromagnetic field. Introducing the particles as described the patient is thereafter subjected to an alternating electromagnetic field to inductively heat the particles sufficiently to raise the temperature of the atherosclerotic lesion and destroy the atherosclerotic lesion without harming the normal artery or intima.

5 Claims, No Drawings

ATHEROSCLEROSIS TREATMENT METHOD

INTRODUCTION

This invention relates generally to a process and composition for the treatment of atherosclerosis in living blood vessels. More particularly, the present invention relates to method and composition for the treatment of atherosclerosis by the destruction of the atherosclerotic lesion without injuring the normal blood vessel.

BACKGROUND OF THE INVENTION

There are presently a number of methods and techniques for the treatment of atherosclerosis among which may be included chemotherapy and surgery. Chemotherapeutic attempts have centered around decreasing serum lipid (cholesterol and triglyceride) levels or altering the metabolism in order to affect the scattered atherosclerotic lesions throughout the body. Surgery is only effective in isolated symptomatic lesions and cannot affect the multitude of atherosclerotic lesions throughout the body.

Theories relating to the etiology of atherosclerosis are many and vary from genetic and ecologic factors to levels of lipids in the bloodstream to injury of the arterial wall.

A safe and effective treatment for atherosclerosis has been the goal of investigators for a substantial period of time. Such a technique, to be successful in the destruction of the arterial lesions must be selective in effect upon the atherosclerotic lesions and produce no irreversible damage to the normal blood vessel. In sum, the treatment of atherosclerosis must selectively differentiate the atherosclerotic portions of the vessel wall from the normal portions of the vessel wall and must selectively destroy the atherosclerotic lesions without affecting the normal vessel.

It has been known that there are certain physical differences that exist between atherosclerotic lesions and a normal blood vessel. One primary physical difference that exists is that atherosclerotic plaques and certain extravascular related lesions (xanthomas, corneal arcus) arise because altered endothelial permeability allows certain macromolecular plasma proteins (which are normally confined to the circulation i.e. lipids) to permeate endothelium and interact with charged components of the connective tissue gel of the vessel wall. The early lesions of atherosclerosis, the fatty streaks and fibrous plaques show evidence of altered permeability in allowing the uptake of protein-bound dyes (trypan blue), colloidal carbon or labeled cholesterol. These substances are taken up by the atherosclerotic lesion but not by the normal blood vessel wall. The normal intima presents a barrier, metabolic or structural, to the influx of serum cholesterol. During atherogenesis this barrier breaks down permitting the entry of blood consituents. This increased permeability has been theorized to be secondary to the release of histamine, kinins, an immunologic reaction or to previous injury or stress. With this increase in permeability there is an uptake of particles normally excluded from the vessel wall.

In addition it has been shown that to a large extent atherosclerotic lesions are monoclonal in nature and result from the overgrowth and excessive proliferation of a single cell line much like a tumor. Profliferation of endothelial and medial smooth muscle cells occurs secondary to trauma or to hyper-chloesterolemia. These proliferating cells take in foreign particles to a high degree.

It is known therefore that the atherosclerotic lesion will take in large amounts of particles secondary to increased permeability. Furthermore the proliferating cells of the atherosclerotic lesion (endothelial and medial smooth muscle cells), phagocytize these particles. The particles are therefore intracellular in these cells of the atherosclerotic lesion as well as being located between the endothelial cell and the internal elastic membrane of the vessel.

OBJECT OF THE INVENTION

It is therefore the purpose and principal object of the present invention to eliminate the atherosclerotic lesions selectively by intracellularly and extracellularly generating a temperature and by changing biophysical characteristics that will resolve the atherosclerotic lesion without affecting the normal vessel.

DESCRIPTION OF THE INVENTION

The present invention achieves a precise increment of heat rise within the atherosclerotic lesion and within the cytoplasm of the cells. The thermal barrier that characteristically exists as the outer membrane or cell wall of the cell is now utilized as a means of retaining the heat produced within the cell, rather than, as in the past preventing any heat build-up within the cell. By raising the temperature of the intracellular particles as well as the particles between the endothelial cells and the internal elastic membrane in the atherosclerotic lesion the atherosclerotic lesion is resolved without affecting the normal vessel.

In accordance with the present invention, there are found to be a number of approaches that can successfully achieve the end result of an intracellular and extracellular heat rise with resolution of the atherosclerotic lesion.

In its simplest and broadest aspect, the present invention contemplates the introduction into the atherosclerotic lesion of a minute particle, such as a ferromagnetic, diamagnetic or a paramagnetic material, and then subjecting the entire body including the normal vessels to a high frequency alternating electromagnetic field.

This principle on which the present invention is based is also grounded upon the known fact that the atherosclerotic lesion has a far greater affinity for particles and for foreign substances such as these minute particles that are to be introduced, than does the normal blood vessel. Electron micrographs have been taken of tissue following the introduction of such particles and clearly illustrate the selective concentration of the particles in the atherosclerotic lesion. This is expected due to the higher permeability of the atherosclerotic lesion and of the proliferating cells of the atherosclerotic lesion.

The particles which are useful in accordance with the present invention, are those such as the ferromagnetic particles compatible with living tissue may be useful. Similarly, the diamagnetic and paramagnetic materials that may be useful include the following; radioactive isotope labeled albumin, fibrinogen and cholesterol and any other diamagnetic and paramagnetic materials compatible with living tissues (in addition any electric or magnetic dipole present or capable of being induced within the cell can be utilized). The particle size of the particles should be not greater than about 1 micron. Preferably particle size would be less than the 1 micron size.

The minute particles described are to be injected intravenously into the patient through the use of any suitable compatible liquid vehicles. Aqueous solutions of any such body-acceptable materials as dextran, dextrose, saline or blood, as well as water alone, can be used. The liquid vehicle should sustain the particles in suspension for the subsequent injection. Concentrations of such body-acceptable materials that may be useful are those that are up to about 50% by weight in water. Usually a solution of about 1% to 10% is adequate. The concentration of the particles in the solution is not critical and is usually in a range between 50 to 75 mg/cc of the solution.

The intravenous injection into the patient generally is in an amount such that between 1 to 10 mg. of the particles per kg of body weight of the patient are injected at one time; however, up to approximately 20–45 mg. total dosage per kg. of body weight is possible. The greater weight of the patient, the higher the permissible dosage. The total amount of the dosage is not critical though 2 to 3 injections, may be injected within a $\geq$ to 72 hour period. The time span for the injections may vary greatly for various patients and for various objectives.

The minute particles contained in the aqueous medium are transported through the bloodstream and have been found to be phagocytized by the cells of the atherosclerotic lesions and the atherosclerotic lesions themselves to a far greater degree than, and in fact in some cases to the possible exclusion of their admittance into normal cells.

Electromicrographs of the atherosclerotic lesions have proven the selective pickup of the magnetic particles.

The next stage of the present invention is to bring about by inductive heating with high frequency alternating electromagnetic field a precise rise in the temperature of the cell and of the atherosclerotic lesion. The principle of inductive heating through the use of hysteresis is a known principle. Similarly, the monitoring of the temperatures of the living cells is a presently available technique well-known to the medical science.

The inductive heating of the minute particles is achieved by using a electronic oscillator operating in the high-frequency range which heats the particles by subjecting them to an intense high-frequency field within a large but otherwise conventional helical coil, field energy being converted to heat through hysteresis losses and the resistive dissipation of eddy currents. The helical inductive coil is of sufficient internal diameter to permit the patient to pass within and of such length to encompass the length of the patient. Generally, the internal diameter should be at least 2 feet, but preferably would be greater than 3–6 feet in diameter. No maximum diameter is known to exist except that required from practical and economical considerations. Diameters of inductive coils of greater than 6 feet have a preferential effect in the overall process by providing a more uniform flux gradient to the patient.

The frequency of the electromagnetic alternating high frequency field will range from 50 kilohertz to 10 megahertz and the power input of the oscillator-generator will range from 0.5 kilowatts to 1.0 kilowatts per kg. of patient body weight 0.75 kilowatts of power per 1.0 kilograms of body weight has been found to be particularly useful. In this power and frequency range, the coil is selected to produce from 400 to 800 oersteds, preferably 550–650 oersteds.

The time necessary to inductively heat the minute particles held within the cells and the atherosclerotic lesions to be treated depends substantially upon the frequency and the power producing the alternating electromagnetic field and ultimately the strength of the field produced. In general, it has been found that subjecting the patient to 5 to 12 minutes or preferably 8 to 10 minutes of the alternating elecromagnetic field would be adequate to resolve the atherosclerotic lesion. It should be clearly understood that the variables with respect to the type and concentration of the particles in the vehicle and the electromagnetic treatment are not critical provided that the necessary temperature is achieved.

EXAMPLE I

As a specific example of the simplest form of the present invention, ferric hydroxide particles of 0.7 micron size are suspended in a 5% dextrose aqueous solution in an amount of about 50 mg. of the particles per cc. Dosages in the amount of 30 mg. per kg. of body weight each of the particles should be made twice, by intravenous injections, each being 24 hours apart. The patient is then ready for the electromagnetic treatment by insertion entirely within an inductive coil 3 feet in diameter. The coil is connected to an alternating current generator, producing a frequency of 3 megahertz and a field of 600 oersteds. The patient is to be subjected to the electromagnetic treatments about 6 hours after the last injection. The inductive heating of the particles within the atherosclerotic lesion is between 8 and 10 minutes during which time the temperature within the cells will have increased 8.5° centigrade. At this temperature the proliferating cells within and the atherosclerotic lesion itself will be resolved while the normal vessel is unaffected.

While the simplest aspect of the invention has been described in detail, the selectivity of the magnetic particles for the atherosclerotic lesions may be increased through the use of several techniques.

The addition of an atherosclerotic seeking agent such as radioisotope labelled substances or a specific anitbody is useful in directing the minute particles more selectively to the atherosclerotic lesions. It is known that radio-isotope labelled albumin, fibrinogen and chloesterol as well as antibodies have an affinity for and are taken up by atherosclerotic lesions. It is also possible that the radio-isotopes may be used to substitute for the magnetic particles and be injected intravenously so as to be selectively taken up by the atherosclerotic lesions. Many of these radio-isotopes are inherently paramagnetic or diamagnetic and whether chemically or physically combined with other particles or used alone the effect of the alternating electromagnetic field upon the magnetic particles and/or the radio-isotopes would be to raise the temperature of the atherosclerotic lesions. Typical examples of useful radio-isotopes are: I-131 albumin, I-131 fibrinogen, $H^3$cholesterol, technetium-99 m. A great many other radioisotopes are useful and the above are only examples. The size and concentration of the radioisotopes alone or attached to the minute particles and the manner of injection is precisely the same as previously described.

These radioisotopes or antibodies may be bound to the particles as iodine-131 (the radioisotope) has been bound to albumin for lung scanning in the past. Antibodies, for instance, may be attached to the ferromagnetic, paramagnetic, or diamagnetic particles by use of an intermediate reducing glucose unit or its derivation such as metasaccharinic acid, in a conventional manner and as described in Example III, much as high molecular weight dextran is bound to ferric hydroxide.

It is known that antibodies can be formed by injection of lipoproteins removed from one patient with atherosclerosis and injected into another patient. These antibodies can then be selectively isolated and have usefulness in the present invention as a selective atherosclerotic lesion cell seeking agent.

These antibodies may be bound chemically or physically to the minute particles and then re-injected into the patient to be treated. Due to the antibodies' specificity for the original atherosclerotic lesion, the antibodies bound to the particles will even more selectively induce the particles to be phagocytized by the atherosclerotic lesion.

Antibodies with radioactive isotopes may be produced by feeding the animals producing the antibodies, labeled amino acids. This labeled amino acid is then incorporated into the antibody.

Large chemical entities can be attached to antibody molecules. Large proteins may be attached via diagotized atoxyl (p-amino-benzene arsenic acid). Antibodies may be bound while they are attached to a hapten or to an antigen. This protects the immunologically specific site of the antibody during the binding procedure.

There does not appear to be any danger in an increased concentration of the particles in the normal vessel in view of the phagocytic charcteristics of the atheroclerotic lesion but to efficiently use all of the magnetic particles and to permit the smallest dosage possible, it is desirable to utilize where beneficial a selective atherosclerotic seeking agent such as the radioisotopes or the antibodies. In this manner, an even greater concentration of the magnetic particles should be found in the atherosclerotic lesion and a very minor amount if not an exclusion of such particles in the normal vessel.

A specific example of the use of a radioisotope in accordance with the present invention is as follows.

EXAMPLE II

I-131 Albumin is incorporated into a sterilized isotomic 5% saline solution the concentration being 75u C./cc and the dosage being 15u C./kg body weight. Upon injection a 6 hour period is allotted for the I-131 albumin to isolate itself and selectively concentrate within the atherosclerotic lesion. Thereafter the same alternating electromagnetic field is applied in exactly the same manner as previously described in Example I. This produces resolution of the atherosclerotic lesion.

When the I-131 albumin is to be utilized as an atherosclerotic seeking agent it may be bound to the particle. This combined particle may be injected into the patient in precisely the same manner and it would be found that the I-131 albumin selectively delivers the particle to the atherosclerotic lesions. Thereafter when the atherosclerotic lesions are subjected to the alternating electromagnetic field, the atherosclerotic lesions are selectively destroyed.

It is also possible that the known utility of specific anti-atherosclerotic agents such as the chemotherapeutic agents, the radioisotopes or specific antibodies may be utilized in accordance with the present invention. For example, chemotherapeutic agents include antihistamines, C-AMP phosphodiesterase inhibitors or enzyme blocking agents (to block elastose, collagenase, hyaluronidase, trypsin, and B-glucuronidase which increase the permeability of the atherosclerotic lesion). It is an aspect of the present invention that such known chemotherapeutic agents in a size less than 1 micron may be coated with ferromagnetic material to produce a total particle of a size less than the approximate 1 micron particle size. The particles in effect encapsulate the chemotherapeutic agent and form a micro-sphere around the chemotherapeutic agent. The coating thickness of the magnetic particle should be approximately 0.1 micron. Thus, the size of the chemotherapeutic agent particle should be about 0.1 micron or less in order to bring about the total particle size of not greater than 1 micron and preferably less.

EXAMPLE III

The following is an example of coating C-AMP with a ferromagnetic material: C-AMP known to make the endothelial membrane less permeable to lipids is taken in a solid state and pulverized into particles 0.5 micron in size. These particles, in turn, are then coated with ferric hydroxide approximately 0.1 micron in thickness, in accordance with any of the conventional methods of coating submicron particles as described in U.S. Pat. No. 3,294,686.

These particles are then colloidally suspended in a 6% by weight aqueous dextran solution. This solution is introduced intravenously to the patient with the result that due to the phagocytic characteristics of the atherosclerotic lesion most of these particles will be deposited in the cytoplasm inside the atherosclerotic lesions' cells. This would take place about 4 to 8 hours after the intravenous injection. After the particles' deposition into the cytoplasm, the ferric hydroxide is acted upon by the cytoplasm and is converted to an organic iron complex (ferritin) which is then absorbed.

After approximately 24 hours, the ferric hydroxide coating is thus solubilized and the chemotherapeutic agent C-AMP is released within the atherosclerotic lesion where it can effectively resolve the atherosclerotic lesion. Time is not critical, and may vary from 1 to 48 hours or more. The other atherosclerotic specific agents may be similarly utilized.

EXAMPLE IV

The chemotherapeutic agent as encapsulated in a ferromagnetic material, as described in Example III, may be injected in precisely the same manner and alternatively subjected to the high frequency alternating electromagnetic field of Example I which then is capable of breaking up the micro-sphere of the magnetic material by a vibrational frequency produced by the electromagnetic field at which the outer surface resonates and its integrity is destroyed. Upon breakup of the micro-spheres the chemotherapeutic agent is released intracellularly and selectively within the atherosclerotic lesions. The same example may be applied in the same manner to the atherosclerotic specific agents.

EXAMPLE V

The encapsulating material may also contain a low melting solid such as wax. This wax is in combination with the ferromagnetic material and applied as in Example III. In this alternative embodiment the application of the alternating electromagnetic field, as in Example I, would melt the low melting solid due to the induction heating of the ferromagnetic material and release the chemotherapeutic agent within the atherosclerotic lesion. Similarly, the other atherosclerotic agents may be similarly utilized.

As previously stated, an atherosclerotic seeking agent such as the radioisotope or antibodies may be utilized to more selectively direct the micro-sphere containing the chemotherapeutic agent to the atherosclerotic lesions. As is known, chemotherapeutic agents sometimes have adverse side effects upon normal cells, but the present procedure would selectively release the chemotherapeutic agent intracellularly and selectively. Compared to the presence of the chemotherapeutic agent in the atherosclerotic lesion, the concentration of the chemotherapeutic agent in the normal cell would be minimal. The undesirable side effects upon the normal cells should therefore be greatly minimized if not totally avoided.

A further embodiment of the present invention which typifies the broad nature of the invention is the incorporation of any atherosclerotic specific antibody or radioisotope within the encapsulating ferromagnetic microsphere in the manner previously described in Example III. Thereafter the antibody or radioactive isotope so coated may be introduced within the atherosclerotic lesion and the alternating electromagnetic field applied as in Example IV to cause the micro-spheres of the ferromagnetic material to release the antibody or the radioisotope intracellularly. It is also possible that the release of the encapsulated material may be by solubilizing the spheres within the cell, as previously described in Example III. A localized field may also be utilized to localize the particles or micro-spheres in particular atherosclerotic lesions.

One of the important features of the present invention is that there is destruction of the atherosclerotic lesions wherever they are located in the patient.

There are many variations of the invention as described and this invention should be limited solely by the scope of the following claims.

I claim:

1. A process for the treatment of atherosclerosis in living tissue by application of external electromagnetic energy capable of the generation of heat and the alteration of biophysical properties intracellularly and extracellularly to induce resolution of atherosclerotic lesions comprising:

intravenously injecting into the patient minute ferromagnetic, paramagnetic or diamagnetic particles capable of being inductively heated and of size less than 1 micron, selectively absorbing said minute particles intracellularly and extracellularly into the atherosclerotic lesion, subjecting the patient to an alternating electromagnetic field to inductively heat and alter the biophysical properties of the minute particles and thereby the atherosclerotic lesions, continuing the inductive heating of said particles to resolve the atherosclerotic lesions.

2. The process of claim 1 wherein the particles are selected from ferric hydroxide and iron oxide.

3. The process of claim 1 including providing an atherosclerotic seeking agent exclusive of said particles in a concentration sufficient to combine with and selectively direct the particles to the atherosclerotic lesion.

4. The process of claim 4 wherein said atherosclerotic seeking agent is an atherosclerotic specific antibody.

5. The process of claim 1 including the use of a localized field to localize the particles in a specific area prior to treatment.

* * * * *